United States Patent [19]

Takahashi

[11] Patent Number: 4,673,264
[45] Date of Patent: Jun. 16, 1987

[54] OPHTHALMIC INSTRUMENT HAVING FOCUS DETECTING MARK PROJECTING MEANS

[75] Inventor: Susumu Takahashi, Tokyo, Japan

[73] Assignee: Tokyo Kogaku Kikai Kabushiki Kaisha, Tokyo, Japan

[21] Appl. No.: 582,330

[22] Filed: Feb. 22, 1984

[30] Foreign Application Priority Data

Feb. 25, 1983 [JP] Japan ................... 58-30461

[51] Int. Cl.[4] .............................. A61B 3/10
[52] U.S. Cl. .................... 351/211; 351/206; 351/208
[58] Field of Search .............. 351/206, 211, 208

[56] References Cited

U.S. PATENT DOCUMENTS 4,293,198 10/1981 Kohaykawa et al. .............. 351/211
4,400,070 8/1983 Isono et al. ......................... 351/211

FOREIGN PATENT DOCUMENTS

57-125732 8/1982 Japan .

Primary Examiner—Rodney B. Bovernick
Assistant Examiner—R. Dzierzynski
Attorney, Agent, or Firm—Brumbaugh, Graves, Donohue & Raymond

[57] ABSTRACT

An eye fundus camera having an automated focus control system which includes a mark projecting system for projecting a focus detecting mark to the retina of a patient's eye to produce a mark image and a photoelectric system for detecting the mark image to judge the focus condition. The photoelectric system produces electric signals which are compared with a threshold level signal to produce mark image signals. In order to ensure an accuracy of detection of the mark image, the threshold level can be changed when it is judged as inappropriate.

6 Claims, 13 Drawing Figures

OPHTHALMIC INSTRUMENT HAVING FOCUS DETECTING MARK PROJECTING MEANS

BACKGROUND OF THE INVENTION

1. Field of the Invention

The present invention relates to detecting means for ophthalmic instruments. More specifically, the present invention pertains to means for detecting images of marks projected to patients' eyes by ophthalmic instruments.

2. Description of Prior Art

Hithertofore, it has been proposed in the field of ophthalmic instruments to project an image of a mark to the retina of the patients' eye so that the focus condition of the photographing optical system of the instrument can be judged by the projected image of the mark. There has further been proposed to detect the projected mark image electrically by producing electric signals corresponding to beams of light from the retina of the patients' eye to which the mark image is projected and slicing the electric signals by a predetermined threshold level to detect the electric signals corresponding to the projected mark image. Such electric signals representing the mark image may be utilized for example in an automated focusing system. It should however be noted that the electric signals as produced by the light beams from the eye retina vary in levels and S/N ratios depending on the reflectivity of the retina, the intensity of the illuminating system and/or various other factors. Such variations can cause inaccuracy in the detection of the mark image and lead to a decrease in the reliability of the automated focusing.

DESCRIPTION OF THE INVENTION

Object of the Invention

It is an object of the present invention to provide signal detecting means for ophthalmic instruments which is substantially free from influences of changes in reflectivity of the eye retina or in the intensity of the illuminating light.

Another object of the present invention is to provide signal detecting means for ophthalmic instruments which can accurately detect signals such as projected mark images.

According to the present invention, the above and other objects can be accomplished by an ophthalmic instrument including an observing optical system having objective lens means adapted to be placed opposite to a patients' eye, a mark projecting optical system for optically projecting a mark through pupil to retina of the patients' eye to produce a mark image at the retina, said mark projecting optical system including focusing means for adjusting focus condition of the mark image, signal detecting electrical means for detecting the mark image and producing an electric signal corresponding to the mark image, level setting means for producing a level signal corresponding to selected one of a plurality of signal levels, mark image discriminating means for comparing the electric signal from the signal detecting electrical means with the level signal to produce a mark image signal when the signal from the signal detecting electrical means is greater than the level signal, means for selecting a desired one of the plurality of signal levels in the level setting means. As an example, the present invention is applicable to an automated focusing system of an eye fundus camera. Where the present invention is applied to an eye fundus camera, the focusing means of the mark projecting means may be interconnected with the focusing optical means of the observing optical system so that the mark projecting means and the observing optical system are simultaneuosly focused. Electrical focus control means may then be provided for controlling the focusing optical system in accordance with the mark image signal so as to obtain automatically a focused condition.

According to the present invention, the signal selecting means makes it possible to change the level signal so that the electric signal corresponding to the projected mark image is distinguished from the signals corresponding to the background light which is a reflection at the retina of the light other than the mark projecting light, by appropriately selecting the signal level in accordance with the reflectivity of the retina or other factors which have influences on the background light.

DESCRIPTION OF PREFERRED EMBODIMENT

Figure 1:
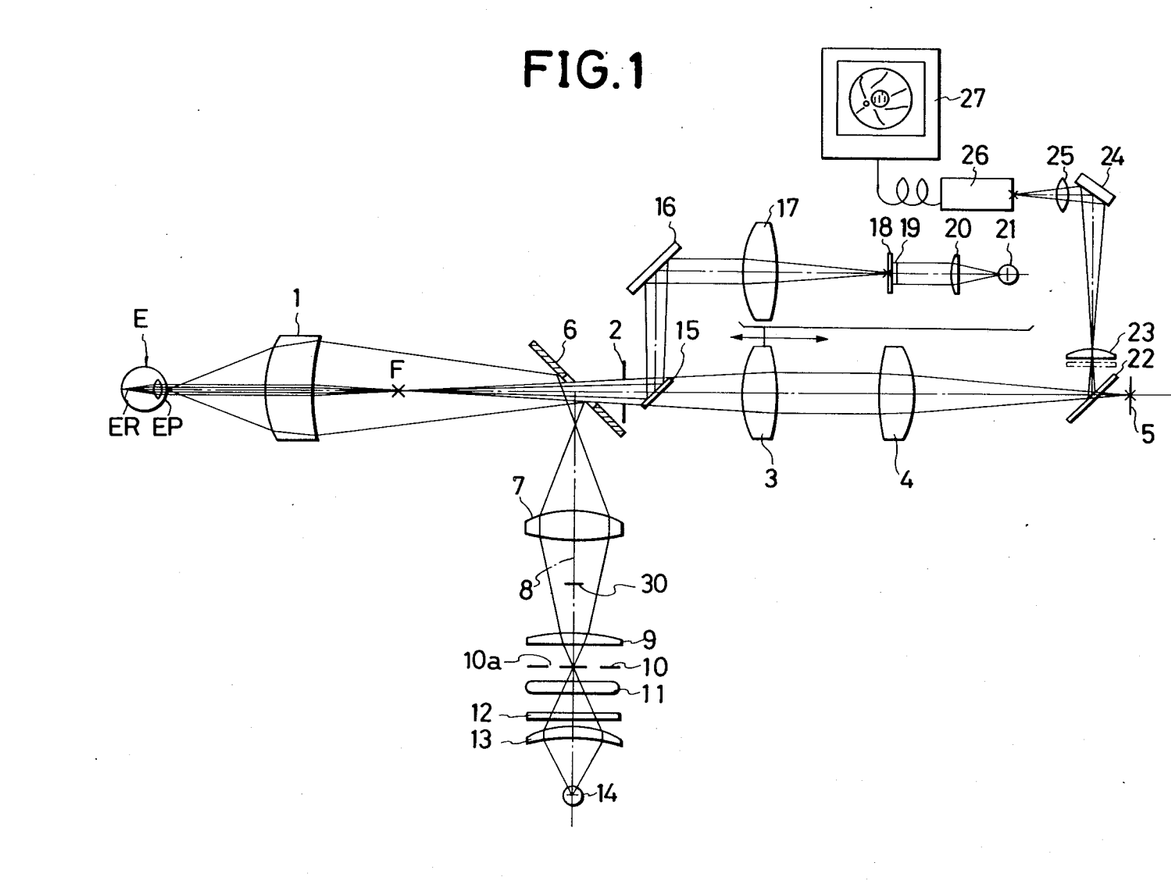
FIG. 1 is a diagrammatical illustration of an optical system of an eye fundus camera in which the present invention can be embodied.

Referring now to the drawings, particularly to FIG. 1, there is shown an optical system of an eye fundus camera which includes an observing or photographing optical system comprising an objective lens 1 adapted to be placed opposite to a patient's eye E. On the optical axis of the objective lens 1, there is an aperture plate 2 located conjugate with the pupil EP of the patient's eye with respect to the objective lens 1. The photographing optical system further includes a focusing lens 3, an imaging lens 4 and a photographing film 5 which are arranged in this order along the optical axis of the objective lens. The lenses 3 and 4 are arranged so as to form an afocal optical system. In the photographing optical system, an image of the retina ER of the patient's eye E is once produced at the point F and then at the film 5.

In front of the film 5, there is obliquely provided a retractable mirror 22. Along the reflecting optical path of the mirror 22, there is a field lens 23 which has an image plane substantially conjugate with the photographing film 5. The light beam which has passed through the imaging lens 4 is therefore reflected by the mirror 22 to produce an image of the retina ER on the field lens 23. The image is then relayed through a mirror 24 and an imaging lens 25 to a photoelectric surface of a TV camera 26 which produces a signal for producing an visible image on a monitor TV.

The eye fundus camera further includes an illuminating optical system which includes an illuminating light source 14 and a photographing light source 11. Between the illuminating light source 14 and the photographing light source 11, there is located a condenser lens 13 and a heat-blocking filter 12. The light from the light source 11 or 14 is passed through a ring-shaped aperture 10a of an aperture plate 10, then through a condenser lens 9 and a relay lens 7 along the illuminating optical axis 8 which intersects the optical axis of the objective lens 1. On the optical axis of the objective lens 1, there is obliquely provided an apertured mirror 6 which is substantially conjugate with the pupil EP of the patient's eye E. The illuminating light which has passed through the aperture 10a produces an image of the aperture 10a on the reflective surface of the mirror 6 and reflected toward the patient's eye to form an image of the aperture 10a in the pupil EP and then illuminate the retina ER.

The eye fundus camera further includes a mark projecting optical system for the purpose of focusing. The system includes a light source 21 and a condenser lens 20 which define a mark projecting optical path. In the mark projecting optical path, there is a mark plate 18 combined with light deflecting prisms 19. The light which has passed through the mark plate 18 is passed through a relay lens 17, reflected by mirrors 16 and 15 to proceed through the aperture plate 2 and the aperture in the apertured mirror 6 to the objective lens 1. The mark projecting light is then passed through the objective lens 1 and the pupil EP of the patient's eye E to the retina ER.

Figure 2A:
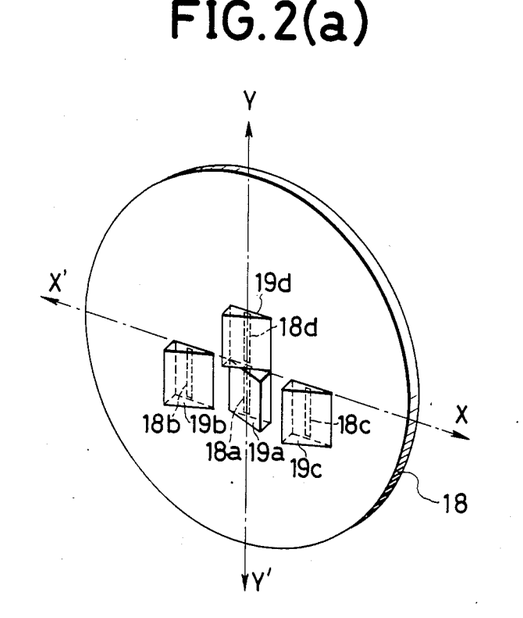
FIG. 2(a) is a perspective view of a mark plate adopted in the mark projecting system of the eye fundus camera.

Referring to FIG. 2(a), it will be noted that the mark plate 18 has a mark comprised of a pair of slits 18a and 18d aligned along a vertical line Y—Y' and a further pair of slits 18b and 18c which are parallel with the slits 18a and 18d but spaced from the vertical line Y—Y' by the same distance in the opposite directions. The deflecting prisms include prisms 19a, 19b, 19c and 19d which are associated respectively with the slits 18a, 18b, 18c and 18d. The prisms 19a, 19b, 19c and 19d functions to deflect the light beams passing through the slits 18a, 18b, 18c and 18d in the directions shown by arrows a, b, c and d, respectively. As described previously, the light beams which have passed through the slits 18a, 18b, 18c and 18d in the mark plate 18 are passed through the relay lens 17 and then reflected by the mirrors 16 and 15, the light beams then pass through the aperture plate 2 and the aperture in the mirror 6 to form images of the slits at the position F. The slit images are then relayed through the objective lens 1 and the pupil EP of the eye E to the retina ER.

Figure 2B:
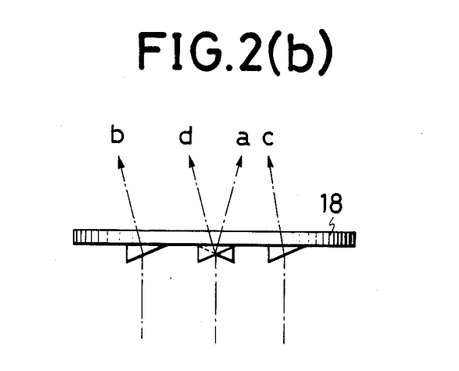
FIG. 2(b) is a top plan view of the mark plate showing paths of mark projecting light beams.
Figure 3:
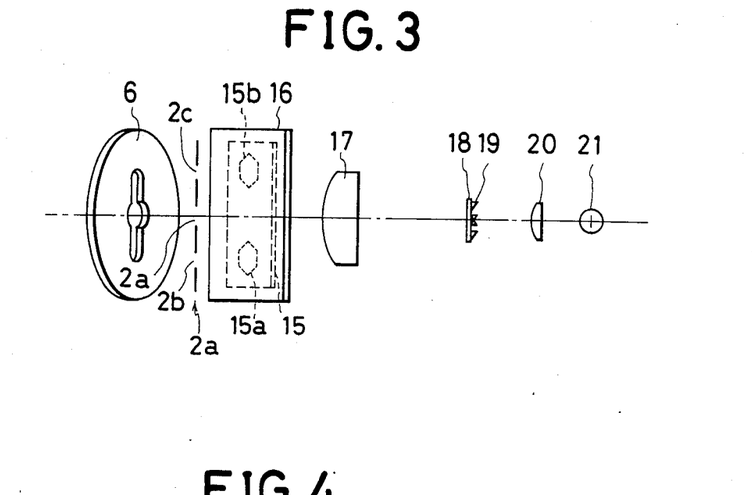
FIG. 3 shows an example of the mark projecting system.

The mark projecting beams are divided into two directions as shown in FIG. 2(b). In order to reflect these beams toward the objective lens 1, the mirror 15 has a pair of reflective surfaces 15a and 15b which are positioned symmetrically with respect to the optical axis of the objective lens 1 (FIG. 3). With this structure of the mirror 15, it does not disturb the light which has emitted from the eye retina ER and passed through the objective lens 1 to the observing optical system. As shown in FIG. 3, the aperture plate 2 has a central aperture 2a for passing the observing lightbeam and a pair of apertures 2b and 2c for passing the mark projecting light beams. It will also be seen in FIG. 3 that the aperture of the mirror 6 is of a sidewardly elongated configuration.

In order to increase the contrast of the mark image at the retina, it is desirable to block the background illumination at the area where the mark image is projected. For the purpose, the illustrated eye fundus camera includes a retractable opaque plate 30 in the illuminating optical system. The plate 30 is located substantially conjugate with the retina ER of the patient's eye E and has a diameter sufficient to cover the mark image.

In the optical system shown in FIG. 1, the relay lens 17, the mark plate 18, the deflecting prisms 19, the condenser lens 20 and the light source 2 of the mark projecting system are assembled so that they are moved as a unit along the projecting optical axis and the assembly is interconnected with the focus lens 3 in the observing optical system so that they move together. Thus, the focus condition of the observing optical system can be judged by the focus condition of the projected mark image.

Figure 4:
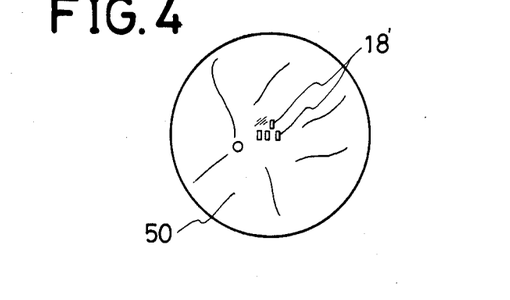
FIG. 4 shows an image of eye fundus as produced on the monitoring TV.
Figure 5A:
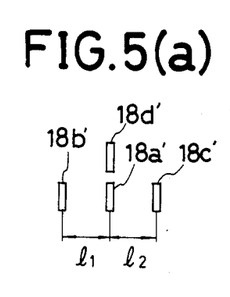
FIGS. 5(a), (b) and (c) show mark images under different focus conditions.
Figure 5B:
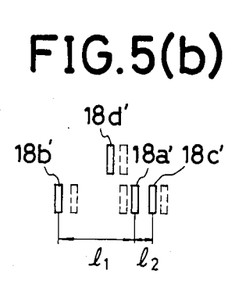
Figure 5C:
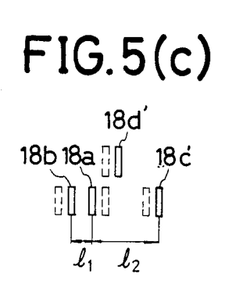

With the arrangement described above, there is displayed in the monitoring TV 27 an image 50 of the retina ER with an image 18' of the mark superposed thereon as shown in FIG. 4. The relationship between the focus condition and the position of the mark image is shown in FIG. 5. In FIG. 5(a), there are shown images 18a', 18b', 18c' and 18d' of the mark slits 18a, 18b, 18c and 18d in the focused condition. FIGS. 5(b) and (c) show the images under out-of-focus conditions. In FIGS. 5(b) and (c), the locations of the mark slit images in focused condition are shown by dotted lines for reference. Where the focal plane of the mark slit images is offset from the retina ER in the direction of the optical axis of the objective lens 1, the mark slit image 18a' is displaced in a direction opposite to the direction of displacement of the mark slit images 18b', 18c' and 18d'. Under a focused condition, the spacing $l_1$ between the slit images 18a' and 18b' is equal to that $l_2$ between the slit images 18a' and 18c'. It will therefore be understood that, by detecting the spacings $l_1$ and $l_2$ as electric signals, it becomes possible to know the focus condition of the observing and photographing optical system.

Figure 6:
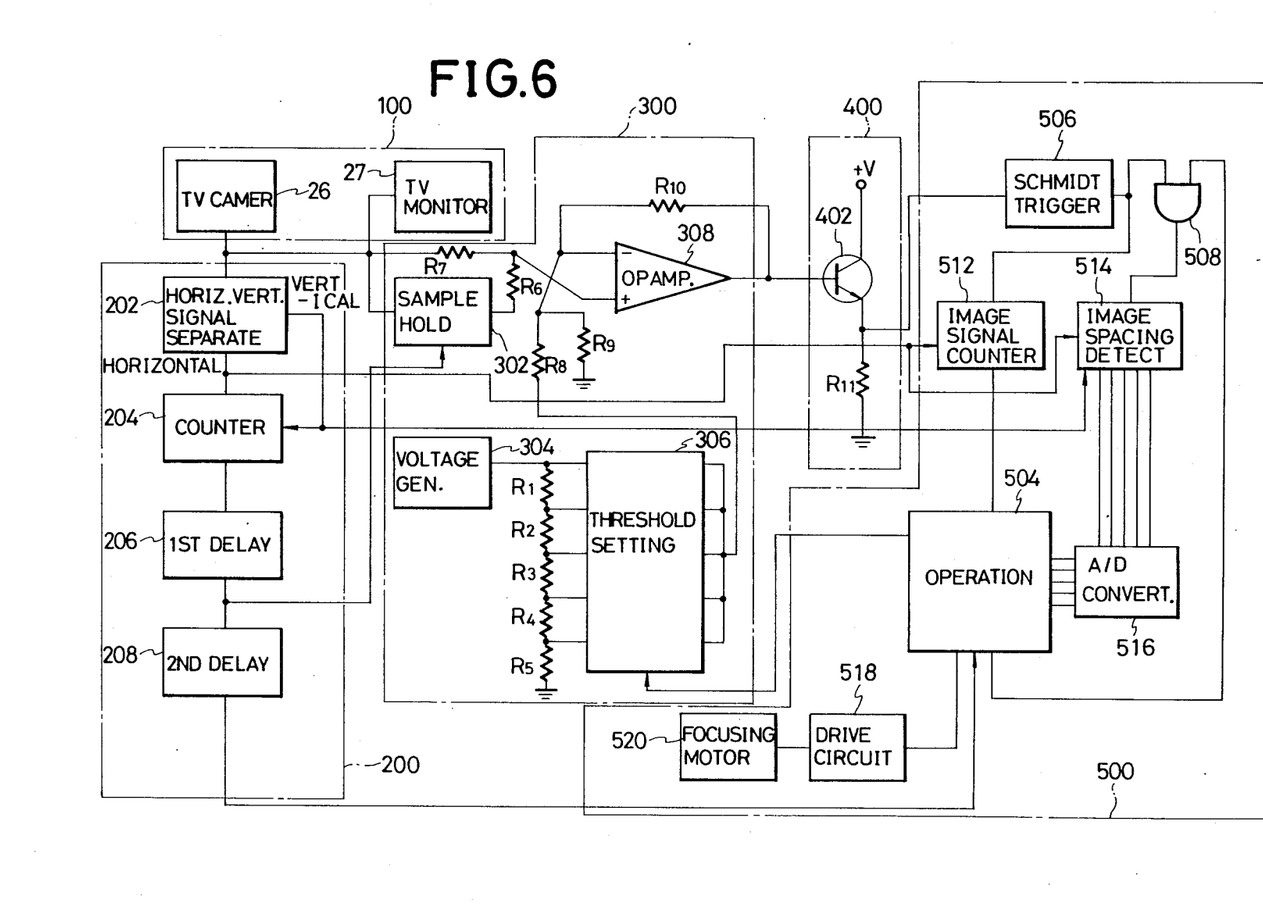
FIG. 6 is a circuit diagram of an electric system including a signal detecting circuit in accordance with one embodiment of the present invention.

Referring now to FIG. 6, there is shown an electric circuit for processing electric signals which are obtained in the monitoring TV 27 from the images of the retina and the projected mark slits. The circuit includes an image forming section 100, a timing signal section 200, a threshold level setting section 300, a buffer section 400 and an automatic focusing section 500.

The image forming section 100 is comprised of the TV camera 26 and the monitoring TV 27 which produce the image 50 of the retina superposed with the image 18' of the projected mark as already described.

The timing signal section 200 includes a horizontal and vertical synchronous signal separating circuit 202, a counter 204 a first time delay circuit 206 and a second time dealy circuit 208. The separating circuit 202 is connected with the TV camera 26 to receive image signals therefrom and functions to separate horizontal synchronous signals from vertical synchronous signals. The horizontal and vertical synchronous signals are respectively applied to the counter 204 so that the numbers of the horizontal synchronous signals are separately counted.

Figure 7:
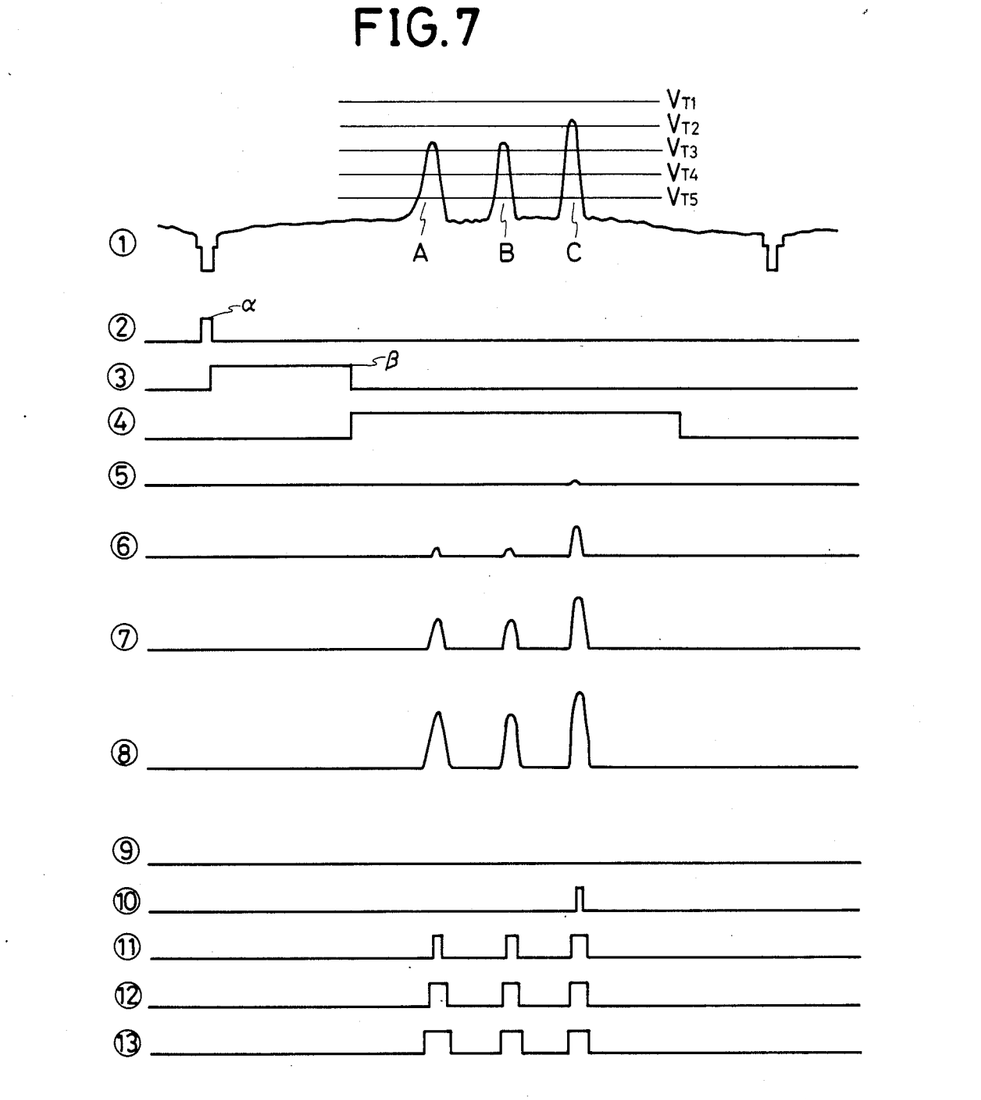
FIG. 7 shows signal wave patterns which will be produced in the circuit shown in FIG. 6.

The counter 204 counts the horizontal synchronous signals and produces a signal α as shown in FIG. 7(2)

when a predetermined number is counted. The predetermined count number corresponds to the number of horizontal scanning lines in the TV camera which include mark slit image signals. The output of the counter 204 is applied to the first time delay circuit 206. The vertical synchronous signals are used to clear the counted values of the counter 204.

The first time delay circuit 206 produces a signal $\beta$ which starts as shown in FIG. 7(3) at the end of the signal $\alpha$. The duration of the signal $\beta$ is determined so that the end of the signal $\beta$ always comes before the projected mark slit signals A, B and C as shown in FIG. 7(1) under any circumstances within the range of displacement of the slit images. The output of the first time delay circuit 206 is applied to the second time delay circuit 208 and a sample-hold circuit 302. The second time dealy circuit 208 produces a signal which starts as shown in FIG. 7(4) at the end of the signal $\beta$. The duration of the output from the second time delay circuit 208 is determined so that is covers the range in which the mark slit images A, B and C are displaced.

The threshold level setting section 300 includes a sample-hold circuit 302 which is connected with the TV camera 26 to receive image signals therefrom. Further, the circuit 302 receives a signal from the first time delay circuit 208 so that is allows the iamge signals when the high level signals as shown in FIG. 7(3) is received from the circuit 206 and maintains the image signal at the end of the high level signal from the circuit 206 in the period wherein the high level signal is not received from the circuit 206.

The section 300 includes a voltage generator 304 which produces an electric voltage which is slightly higher than the highest level of the mark slit image signals. The output of the voltage generator 304 is connected with a voltage divider comprised of resistors R1, R2, R3, R4 and R5 and the voltage divider is connected with a threshold level setting circuit 306.

The output of the sample-hold circuit 302 is connected through a resistor R6 with the positive input terminal of the operation amplifier 308. The positive input terminal of the operation amplifier 308 is also connected through a resistor R7 with the TV camera 26. The operation amplifier 308 has a negative input terminal which is connected through a resistor with the output of the threshold level setting circuit 306. The negative input terminal is further grounded through a resistor R9. The operation amplifier 308 has an output terminal connected through a resistor R10 with the negative input terminal thereof so as to provide the amplifier with a differential amplifying function. Thus, when the output level $V_T$ of the threshold level setting circuit 306 is changed as shown by $V_{T1}$, $V_{T2}$, $V_{T3}$, $V_{T4}$ and $V_{T5}$ in FIG. 7(1), the output of the operation amplifier 308 is changed. FIGS. 7(5) through (8) show the outputs of the operation amplifier 308 with the threshold levels $V_{T2}$, $V_{T3}$, $V_{T4}$ and $V_{T5}$, respectively.

The buffer section 400 includes a transistor 402 having an emitter grounded through a resistor R11. The base of the transistor 402 is connected with the output of the operation amplifier 308 whereas the collector is connected with a power source.

The automatic focusing section 500 includes an operation circuit 504, a schmidt trigger circuit 506, a first AND circuit 508, a mark slit image counter 512, a mark slit image spacing detecting circuit 514, an analique-digital (A/D) converter 516, a focusing drive circuit 518 and a focusing motor 520. The section 500 functions to count the number of the mark slit images and perform an automated focus control under the vertical and horizontal synchronous signals from the circuit 202 and the signal from the circuit 208.

The schmidt trigger circuit 506 is connected with the emitter of the transistor 400 to convert the analogue signals from the buffer section 400 into rectangular signals as shown in FIGS. 7(9) through (13). The output of the schmidt trigger circuit 506 is applied on one hand to the mark slit image counter 512 and on the other hand to the spacing detecting circuit 514 through the first AND circuit 508. The counter 512 is also connected with the output of the circuit 202 to receive the horizontal synchronous signals therefrom. The output of the schmidt trigger circuit 506 is counted by the counter 512 and the counter value is cleared by the horizontal synchronous signal from the circuit 202. The counted value is applied from the counter 512 to the operation circuit 504 at the end of the signal from the second time delay circuit 208. For the purpose, the output of the second time delay circuit 208 is connected with the operation circuit 504.

Figure 8:
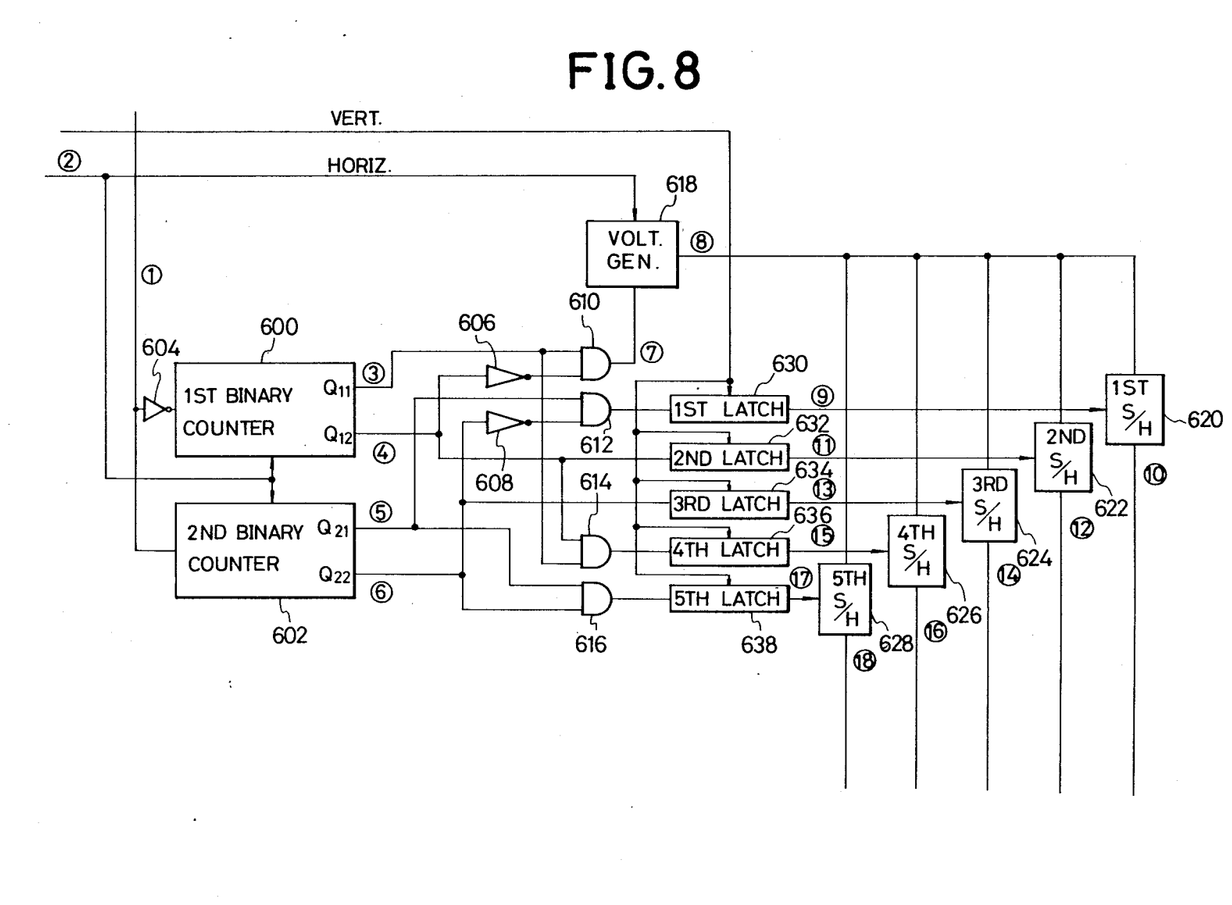
FIG. 8 is a circuit diagram showing the mark image spacing detecting circuit.

The first AND circuit 508 has an input terminal which is connected with the output of the operation circuit 504 so that the output of the schmidt trigger circuit 506 is passed to the spacing detecting circuit 514 selectively in accordance with the output of the operation circuit 504. As shown in FIG. 8, the spacing detecting circuit 514 includes a first binary counter 600 which counts ends of pulse signals, a second binary counter 602 which counts ends of pulse signals, first through third NOT circuits 604, 606, 608, second through fifth AND circuits 610, 612, 614, 616, a voltage generator 618, first through fifth sample-hold circuits 620, 622, 624, 626, 628 and first through fifth latch circuits 630, 632, 634, 636, 638.

Figure 9:
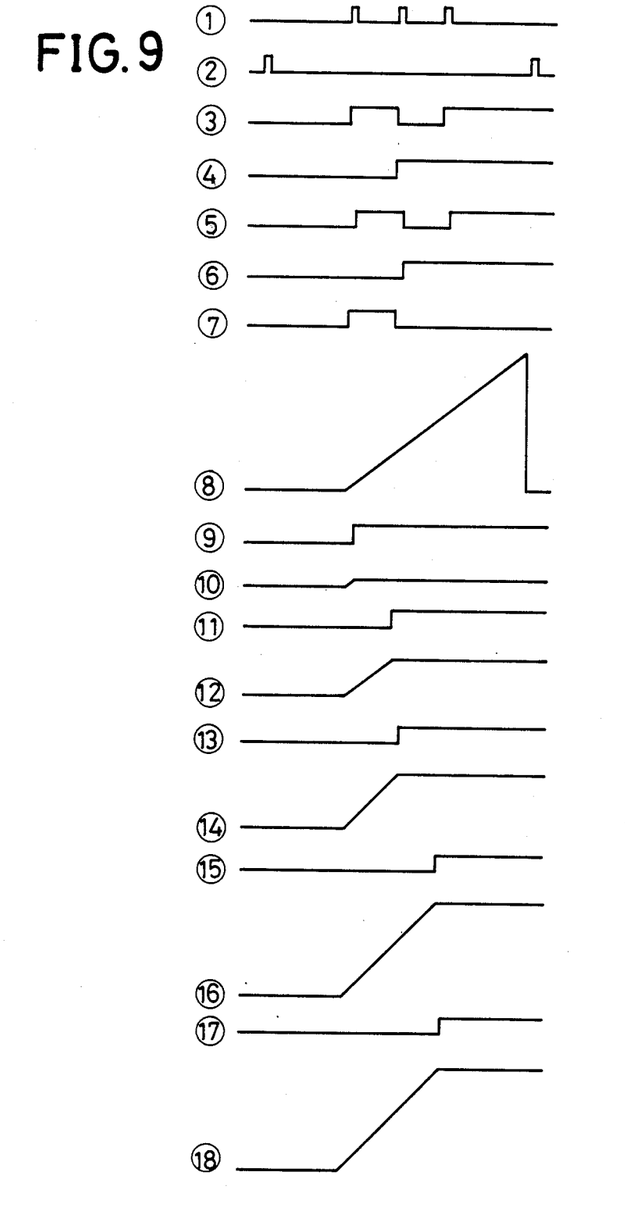
FIG. 9 shows signal patterns in the circuit shown in FIG. 8.

The output signals from the schmidt trigger circuit 506 as shown in FIG. 9(1) are applied through the first AND circuit 508 and the first NOT circuit 604 to the first binary counter 600. Further, the signals from the schmidt trigger circuit 506 is also applied through the first AND circuit 508 to the second binary counter 602. The first binary counter 600 counts the ends of the mark slit image signals and produces an output corresponding to the figure of the lowest digit at the output terminal $Q_{11}$ as shown in FIG. 9(3) and an output corresponding to the figure of the highest digit at the output terminal $Q_{12}$ as shown in FIG. 9(4). Similarly, the second binary counter 602 produces outputs as shown in FIGS. 9(5) and (6) at the output terminals $Q_{21}$ and $Q_{22}$, respectively.

The first and second binary counters 600 and 602 are connected with the circuit 202 to receive horizontal synchronous signals therefrom. These signals are used to reset the counters. The second AND circuit 610 has an input terminal which is connected with the terminal $Q_{11}$ of the first binary counter 600 and another input terminal which is connected with terminal $Q_{12}$ through the second NOT circuit 606 which inverts the signal from the terminal Q12. The second AND circuit 610 produces an output pulse as shown in FIG. 9(7) which starts at the start of the first mark slit image signal. The output of the AND circuit 610 is applied to the voltage generator 618 as the voltage start timing signal.

The voltage generator 618 has a latch function and start to produce a linearly increasing voltage signal as shown in FIG. 9(8) at the start of the first mark slit image signal. The output of the voltage generator 618 is applied to the first through fifth sample-hold circuits 620, 622, 624, 626 and 628. The voltage generator 618 is connected to receive horizontal synchronous signals as shown in FIG. 9(2) from the circuit 202 and the generation of the voltage signal is terminated when the horizontal synchronous signal is received.

The first through fifth latch circuits 630 through 638 produce timing signals respectively for the first through fifth sample-hold circuits 620 through 628. The latch circuits 630 through 638 are connected to receive vertical synchronous signals as release signals and the circuits therefore continue to provide latching function until the vertical synchronous signal is received.

The third AND circuit 612 has an input terminal connected with the output terminal $Q_{21}$ of the second binary counter 602 and another input terminal connected with the output terminal $A_{22}$ through the third NOT circuit 608. The output of the third AND circuit 612 is applied to the first latch circuit 630 which produces a signal as shown in FIG. 9(9). The output of the latch circuit 630 is applied to the first sample-hold circuit 620 as the timing signal. As noted in FIG. 9, the timing signal to the circuit 620 starts at the end of the first mark slit image signal. The first sample-hold circuit 620 holds the input signal when a high level timing signal is received from the latch circuit 630 so that it maintains the voltage signal from the generator 618 at the end of the first mark slit image signal as shown in FIG. 9(10).

The second latch circuit 632 has an input connected with the input terminal $Q_{12}$ of the first binary counter 600 to receive the signal as shown in FIG. 9(4) and produce a timing signal which is shown in FIG. 9(11) and applied to the second sample-hold circuit 622. The timing signal starts at the start of the second mark slit image signal. The second sample-hold circuit 622 holds the input signal when a high level timing signal is received so that it produces an output which is shown in FIG. 9(12) and correspond to the voltage signal as produced by the generator 618 in the period between the start of the first mark slit image signal and the start of the second mark slit image signal.

The third latch circuit 634 has an input terminal connected with the output terminal $Q_{22}$ of the second binary counter 602 to receive a signal which is shown in FIG. 9(6) and starts at the end of the second mark slit image signal. The third latch circuit 634 produce a timing signal which is shown in FIG. 9(13) and applied to the sample-hold circuit 624. Thus, it will be understood that the third sample-hold circuit 614 produces a signal which corresponds to the voltage signal as produced by the generator 618 in a period between the start of the first mark slit image signal and the end of the second mark slit image signal as shown in FIG. 9(14).

The fourth latch circuit 636 has an input connected with the output of the fourth AND circuit 614 which has inputs connected respectively with the input terminals $Q_{11}$ and $Q_{12}$ of the first binary counter 600. The fourth latch circuit 636 therefore produces a timing signal which starts at the start of the third mark slit image as shown in FIG. 9(15) and applied to the fourth sample-hold circuit 626. Thus, the fourth sample-hold circuit 626 produces an output which corresponds to the voltage signal as produced by the generator 618 in a period between the start of the first mark slit image signal and the start of the third mark slit image signal as shown in FIG. 9(16).

The fifth latch circuit 638 has an input converted with the output of the fifth AND circuit 616 which has inputs connected respectively with the output terminals $Q_{21}$ and $Q_{22}$ of the second binary counter 602. Thus, the fifth latch circuit 638 produces a timing signal which starts at the end of the third mark slit image signal as shown in FIG. 9(17). The timing signal is applied to the fifth sample-hold circuit 628 which produces an output corresponding to the voltage signal as produced by the generator 618 in the period between the start of the first mark slit image signal and the end of the third mark slit image signal as shwon in FIG. 9(18).

The output signals of the sample-hold circuits 620 through 628 are maintained until a vertical synchronous signal is received from the circuit 202 since they receive timing signals from the latch circuits 630 through 638 so that a sufficient time is provided for the operation of the A/D converter 512.

The output signals of the first through fifth sample-hold circuits 620, 622, 624, 626 and 628 are applied to the A/D converter 516 which converts the input signals into digital signals. The outputs of the A/D converter 516 is connected with the operation circuit 504.

The operation circuit 504 receives signals of the second time delay circuit 208 of the timing signal section 200, of the mark slit image counting circuit 512 and of the A/D converter 516 and produces a gate signal adapted to be applied to the first AND circuit 508 and a focus control signal adapted to be applied through the driving circuit 518 to the focusing motor 520.

Figure 10:
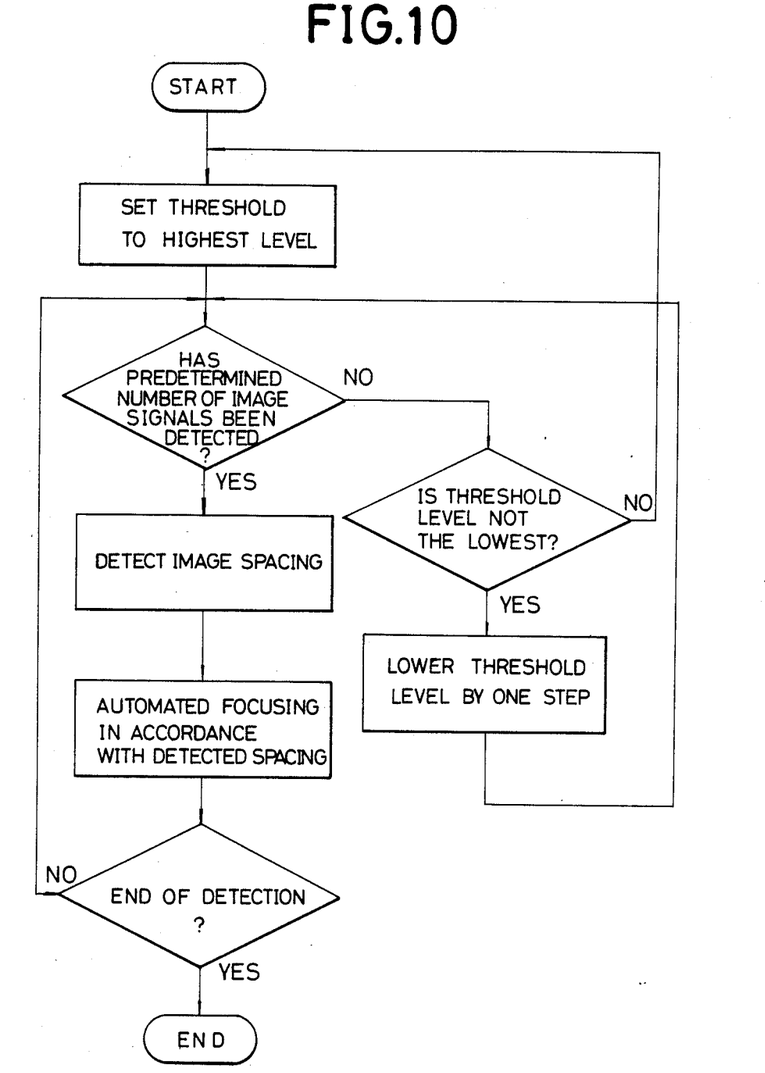
FIG. 10 is a flow chart of automated focus control.

Referring now to FIG. 10 which shows a flow chart of the operation of the automated focusing, the output of the circuit 504 at first adjsuts the threshold level setting circuit 306 so that the highest value $V_{T}1$ of the threshold level is produced. Then, the number of the mark slit image signals is obtained by the signal from the counter 512. In the counter 512, a judgement is made as to whether the predetermined number, for example, three of the image signals are detected. If the predetermined number of slit image signals are not detected, the circuit 504 produces a signal based on the signal from the counter 512 for controlling the threshold level setting circuit 306 to decrease the level by one step. If the threshold level is the lowest, the level is returned to the highest value. The procedure is repeated until the counter 512 detects the predetermined number of mark slit image signals.

When the predetermined number of image signals are detected, the circuit 504 applies a high level signal to the first AND circuit 508 so that the spacing detecting circuit 514 starts to operate. The voltage signals from the first through fifth sample-hold circuits 620, 622, 624, 626 and 628 are converted by the A/D converter 516 into digital signals DA, DB, DC, DD, DE, respectively, and applied to the operation circuit 504. The operation circuit 504 performs calculations to obtain the spacings $l_1$, $l_2$ and $\Delta l$ based on the equations:

$$l_1 = \frac{DB + DC - DA}{2}$$

$$l_2 = \frac{DD + DE - DB - DC}{2}$$

$$\Delta l = l_1 - l_2$$

Then, the circuit 504 produces an output corresponding to the value Δl and applies it to the motor drive circuit 518 to thereby produce a focusing motor drive current. The amount of focus control is determined by the value whereas the direction of the control depending on whether the value Δl is positive or negative.

The invention has thus been shown and described with reference to a specific embodiment, however, it should be noted that the invention is in no way limited to the details of the illustrated arrangements but changes and modifications may be made without departing from the scope of the appended claims.

I claim:

1. An ophthalmic instrument including an observing optical system having objective lens means adatped to be placed opposite to a patient's eye, a mark projecting optical system for optically projecting a mark through a pupil to a retina of the patient's eye to produce a mark image at the retina, said mark image including a plurality of mark segments so that a corresponding number or mark segment images are to be produced at the retina, said mark projecting optical system including focusing means for adjusting focus conditions of the mark image, signal detecting electrical means for detecting the mark image segments and producing an electric signal corresponding to the mark image segments, threshold level setting means for producing a succession of threshold level signals, decreasing in level from an initial level higher than the level of the mark image signals mark image discriminating means for comparing the electric signal from the signal detecting electrical means with each of said threshold level signals to produce a mark image signal when the signal from the signal detecting electrical means is greater than the threshold level signal, means for counting said mark image signals from the mark image discriminating means, means for comparing said count of the mark image signals from the mark image discriminating means with the number of mark image segments, means responsive to said comparison of the mark image signals for selecting the next successive one of the succession of threshold signal levels in the threshold level setting means when said count of the mark image signals from the mark image discriminating means is less than the number of mark image segments, means for determining the distance between the mark image signals when said count of the mark image signals from the mark image discriminating means is equal to the number of mark image segments, and means responsive to said distance determining means for adjusting said focusing means to adjust the focus condition of the mark image.

2. An ophthalmic instrument in accordance with claim 1 in which said observing optical system has focusing optical means movable along an optical axis of the observing optical system, said focusing means of the mark projecting optical system is interconnected with the focusing optical means of the observing optical system so that the mark projecting means and the observing optical system are simultaneously focused.

3. An ophthalmic instrument in accordance with claim 2 in which electrical focus control means is provided for controlling the focusing optical means in the observing optical system in accordance with the mark image signal so as to obtain automatically a focused condition.

4. An eye fundus camera comprising an observing optical system having objective lens means adapted to be placed opposite to a patient's eye and focusing optical means moveable along an optical axis of the observing optical system for focusing, an illuminating optical system for projecting beams of illuminating light to a retina of the patient's eye, a mark projecting optical system for optically projecting a mark through a pupil to the retina of the patient's eye to produce a mark image at the retina, said mark projecting optical system including focusing means movable along an optical axis of the mark projecting optical system, signal detecting photoelectric means for detecting the mark image and producing an electric signal correspodning to the mark image, threshold level setting means for producing a succession of threshold level signals decreasing in level from an initial level higher than the level of the mark image signals, mark image discriminating means for comparing the electric signal from the photoelectric means with the threshold level signal to produce a mark image signal when the signal from the photoelectric means is greater than the threshold level signal, means for determining whether the number of mark image signals from the mark image discriminating means is equal to a predetermined number, means for successively lowering said threshold level when said number of mark image signals is less than said predetermined number, said focusing optical means in the observing optical system being interconnected with the focusing means in the mark projecting optical system so that both optical systems are focused simultaneously, and automated focusing means for controlling the focusing optical means in accordance with the electric signal from the photoelectric means.

5. An eye fundus camera in accordance with claim 4 in which said mark includes a plurality of mark segments which are spaced apart by predetermined spacings so that a corresponding number of mark segment images are to be produced, said judging means including means for counting number of the mark segment images to determine that the threshold level is appropriate when said corresponding number of mark segment images are detected.

6. An eye fundus camera in accordance with claim 5 in which said automated focusing means includes means for detecting spacings of said mark segment images to detect focus condition of the observing optical system.

* * * * *